(12) United States Patent
Jarvik

(10) Patent No.: US 6,472,207 B1
(45) Date of Patent: *Oct. 29, 2002

(54) METHOD FOR PRODUCING TAGGED GENES, TRANSCRIPTS, AND PROTEINS

(75) Inventor: Jonathan W. Jarvik, Pittsburgh, PA (US)

(73) Assignee: Carnegie Mellon University, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/604,037

(22) Filed: Jun. 27, 2000

Related U.S. Application Data (60) Continuation of application No. 08/901,097, filed on Jul. 28, 1997, now Pat. No. 6,080,541, which is a division of application No. 08/000,619, filed on Jan. 5, 1993, now Pat. No. 5,652,128.

(51) Int. Cl.⁷ .................................................. C12N 5/00
(52) U.S. Cl. .................. 435/325; 435/254.11; 435/419; 435/455; 435/471
(58) Field of Search ................................ 435/455, 471, 435/325, 419, 254.11

(56) References Cited

U.S. PATENT DOCUMENTS

| | | | | |
|---|---|---|---|---|
| 5,652,128 A | * | 7/1997 | Jarvik | 435/172.3 |
| 5,916,810 A | * | 6/1999 | Jarvik | 435/440 |
| 6,080,541 A | * | 6/2000 | Jarvik | 435/6 |
| 6,096,717 A | * | 8/2000 | Jarvik | 514/44 |

OTHER PUBLICATIONS

Sugano et al., "Use of an Epitope–Tagged cDNA Library to Isolate cDNAs Encoding Proteins with Nuclear Localization Potential," *Gene*, 120(2), pp. 227–233, 1992.

Pati, "Novel Vectors for Expression of cDNA Encoding Epitope–Tagged Proteins in Mammalian Cells," *Gene*, 114, pp. 285–288, 1992.

Debuchy etal., "The argininosuccinate lyase gene of *Chlamydomonas reinhardtii*: an important tool for nuclear transformation and for correlating the genetic and molecular maps of the ARG7 locus," *The EMBO Journal*, vol. 8, No. 10, pp. 2803–2809, 1989.

Karem et al., "Identification of mutations in regions corresponding to the two putative nucleotide (ATP)–binding folds of the cystic fibrosis gene," *Proc. Nat. Acad. Sci. USA*, vol. 87, pp. 8447–8451, 1990.

Kindle, "High–frequency nuclear transformation of *Chlamydomonas reinhardtii*," *Proc. Natl. Acad. Sco. USA*, vol. 87, pp. 1228–1232, 1990.

(List continued on next page.)

*Primary Examiner*—Scott D. Priebe
(74) *Attorney, Agent, or Firm*—Webb Ziesenheim Logsdon Orkin & Hanson, P.C.

(57) ABSTRACT

The invention described here is a method whereby a molecular tag is put on a gene, transcript and protein in a single recombinational event. The protein tag takes the form of a unique peptide that can be recognized by an antibody or other specific reagent, the transcript tag takes the form of the sequence of nucleotides encoding the peptide that can be recognized by a specific polynucleotide probe, and the gene tag takes the form of a larger sequence of nucleotides that includes the peptide-encoding sequence and other associated nucleotide sequences. The central feature of the invention in its essential form is that the tag-creating DNA has a structure such that when it is inserted into an intron within a gene it creates two hybrid introns separated by a new exon encoding the protein tag. A major virtue of the method is that it allows one to identify new proteins or protein-containing structures, and, having done so, to readily identify and analyze the genes encoding those proteins.

1 Claim, 6 Drawing Sheets

OTHER PUBLICATIONS

Kornfeld et al, "Structure and expression of a family of Ultrabithorax mRNAs generated by alternative splicing and polyadenylation in Drosophila," *Genes & Development,* 3:243–258, pp. 243–258, 1989.

Krasnow et al, "Transcriptional Activation and Repression by Ultrabithorax proteins in Cultured Drosophila Cells," *Cell,* vol. 57, pp. 1031–1043, 1989.

Nilsson et al., "Overlapping Distribution of Two Glycosyltransferases in the Golgi Apparatus of HeLa Cells," *The Journal of Cell Biology,* vol. 120, No. 1, pp. 5–13, 1993.

O'Connor et al., "Alternative RNA products from the Ultrabithorax domain of the bithorax complex," *The EMBO Journal,* vol. 7, No. 2, pp. 435–455, 1988.

Sanger et al., "DNA sequencing with chain-terminating inhibitors," *Proc. Natl. Acad. Sci. USA,* 74, pp. 5463–5467, 1977.

Silflow et al., "*Chlamydomonas reinhardtii* Tubulin Gene Structure," *Annals New York Academy of Sciences,* pp. 18–30, 1986.

Soldati et al., "Intracompartmental Sorting of Essential Myosin Light Chains: Molecular Dissection and In Vivo Monitoring by Epitope Tagging," *Cell,* vol. 66, pp. 277–289, 1991.

Taillon et al, "Mutational Analysis of Centrin: An EF–Hand Protein Associated with Three Distinct Contractile Fibers in the Basal Body Apparatus of Chlamydomonas," *The Journal of Cell Biology,* vol. 119, No. 6, pp. 1613–1623, 1992.

Weber et al., "An SV40 'Enhancer Trap' Incorporates Exogenous Enhancers or Generates Enhancers from Its Own Sequences," *Cell,* vol. 36, pp. 983–992, 1984.

Williams et al, "Molecular Cloning and Sequence Analysis of the Chlamydomonas Gene Doding for Radial Spoke Protein 3: Flagellar Mutation pf–14 is an Ochre Allele," *The Journal of Cell Biology,* vol. 109, pp. 235–245, 1989.

Wilson et al., "The Structure of an Antigenic Determinant in a Protein," *Cell,* vol. 37, pp. 767–778, 1984.

Wright et al., "A Nucleus–Basal Body Connector in *Chlamydomonas reinhardtii* That May Function in Basal Body Localization or Segration," *The Journal of Cell Biology,* vol. 101, pp. 1903–1912, 1985.

Rossant, "Of fin and fur: mutational analysis of vertebrate embryonic development," *Genes & Development,* 6:1, pp. 1–13, 1992.

Dougherty et al., "Determination of Retroviral Vector Mutation Rates and a Promoterless Retroviral Vector," *Gene Transfer Vectors for Mammalian Cells,* pp. 18–23, 1987.

Adams et al., "Complementary DNA Sequencing: Expressed Sequence Tags and Human Genome Project," *Science,* vol. 252, pp. 1651–1656, 1991.

Botstein et al., "Construction of a Genetic Linkage Map in Man Using Restriction Fragment Length Polymorphisms," *American Journal of Human Genetics,* 32(3), pp. 314–331, 1980.

Charbit et al., "Probing the topology of a bacterial membrane protein by genetic insertion of a foreign epitope; expression at the cell surface," *The EMBO Journal,* vol. 5, No. 11, pp. 3029–3037, 1986.

Chen et al., "High–Efficiency Transformation of Mammalian Cells by Plasmid DNA," *Molecular and Cellular Biology,* vol. 7, No. 8, pp. 2745–2752, 1987.

Colbere–Garapin et al., "Patterns of integration of exogenous DNA sequences transfected into mammalian cells of primate and rodent origin," *Gene,* 50(1–3), pp. 279–288, 1986.

Cooley et al., "Insertional Mutagenesis of the Drosophila Genome with Single P Elements," *Science,* vol. 329, pp. 1121–1128, 1988.

Craik et al., "Splice Junctions: Association with Variation in Protein Structure," *Science,* vol. 220, pp. 1125–1129, 1983.

Duyk et al., "Exon trapping: A genetic screen to identify candidate transcribed sequences in cloned mammalian genomic DNA," *Proc. Natl. Acad. Sco. USA,* vol. 87, pp. 8995–8999, 1990.

Field et al., "Purification of a RAS–Responsive Adenylyl Cyclase Complex from *Saccharomyces cerevisiae* by Use of an Epitope Addition Method," *Molecular and Cellular Biology,* pp. 2159–2165, 1988.

Freimuth et al,. "Codon insertion mutants of the adenovirus terminal protein," *Proc. Natl. Acad. Sco. USA,* vol. 83, pp. 7816–7820, 1986.

Freimuth et al., "Introduction of Guest Peptides into *Escherichia coli* Alkaline Phostase,"*The Journal of Biological Chemistry,* vol. 265, No. 2, pp. 896–901, 1990.

Gossler et al., "Mouse embryonic stem cells and reporter constructs to detect developmentally regulated genes," pp. 463–465, 1989.

Green, "Biochemical Mechanisms of Constitutive and Regulated Pre–mRNA Splicing," *Annu. Rev. Cell. Biol.,* pp. 559–599, 1991.

Grimwade et al., "Gene Expression and Protein Localization in Yeast," *16th Int. Conf. on Yeast Genetics and Molecular Biology,* S695, 15–34B, 1992.

Hawkins, "A survey on intron and exon lengths," *Nucleic Acids Research,* vol. 16, No. 21, pp. 9893–9905, 1988.

Hochgeschwender et al., "Identifying Genes Within the Genome: New Ways for Finding the Needle in a Haystack," *BioEssays,* Nol. 13, No. 3, pp. 139–144, 1991.

Lobel et al., "Construction of mutants of Moloney murine leukemia virus by suppressor–linker insertional mutagenesis: Positions of viable insertion mutations," *Proc. Natl. Acad. Sco. USA,* vol. 81, pp. 4149–4153, 1984.

Luehrsen et al., "Insertion of non–intron sequence into maize introns interferes with splicing," *Nucleic Acids Research,* vol. 20, No. 19, pp. 5181–5187, 1992.

Munro et al., "Use of peptide tagging to detect proteins expressed from cloned genes: deletion mapping functional domains of Drosophila hsp70," *The EMBO Journal,* vol. 3, No. 13, pp. 3087–3093, 1984.

Murnane et al., "Recombination events during integration of transfected DNA into normal human cells," *Nucleic Acids Research,* vol. 18, No. 9, pp. 2733–2738, 1990.

O'Kane et al., "Detection in situ of genomic regulatory elements in Drosophila," *Proc. Natl. Acad. Sco. USA,* vol. 84, pp. 9123–9127, 1987.

Rommens et al., "Identification of the Cystic Fibrosis Gene: Chromosome Walking and Jumping," *Science,* vol. 245, pp. 1059–1065, 1989.

Snyder et al., "λgt11: Gene Isolation with Antibody Probes and Other Applications," *Methods in Enzymology,* vol. 154, pp. 107–128, 1987.

* cited by examiner

METHOD FOR PRODUCING TAGGED GENES, TRANSCRIPTS, AND PROTEINS

CROSS-REFERENCE TO RELATED APPLICATIONS

This application is a continuing application of U.S. application Ser. No. 08/901,097, filed Jul. 28, 1997, now U.S. Pat. No. 6,080,541, which is a divisional of U.S. application Ser. No. 08/000,619 filed Jan. 5, 1993, now U.S. Pat. No. 5,652,128.

BACKGROUND—FIELD OF INVENTION

This invention relates to the fields of Molecular Biology and Molecular Genetics with specific reference to the identification and isolation of proteins and of the genes and transcripts that encode them.

BACKGROUND—DESCRIPTION OF PRIOR ART

The primary area of the invention—the identification and tagging of genes and proteins—has received a great deal of attention, and many successful methods have been devised. None of these methods, however, has the feature of tagging gene, transcript and protein in a single event Linkage Analysis. Genes have traditionally been identified by identifying mutations and then mapping them with respect to one another by means of genetic crosses. This kind of mapping, or linkage analysis, does not serve to isolate the genes themselves nor does it indicate anything about the genes' molecular structure or function. In recent years, a form of linkage analysis using restriction fragment length polymorphisms (RFLPs) has come into use. This method serves to identify DNA sequences that are linked to a gene of interest, and, having identified such a DNA sequence, it is possible in principle, and sometimes in practice, to identify and clone the gene itself by performing chromosome walks or jumps. It should be stressed that, even when successful, this strategy identifies the gene, not the protein encoded by the gene.

Transposon Tagging. Another technique for cloning genes that has been developed relatively recently goes by the name transposon tagging. In this technique, mutations due to the insertion of transposable elements into new sites in the genome are identified, and the genes in which the transposons lie can then be cloned using transposon DNA as a molecular probe. Transposon tagging, like RFLP/linkage analysis, identifies genes, not proteins.

Enhancer Trapping. Another method for identifying genes, enhancer trapping, involves the random insertion into a eucaryotic genome of a promotor-less foreign gene (the reporter) whose expression can be detected at the cellular level. Expression of the reporter gene indicates that it has been fused to an active transcription unit or that it has inserted into the genome in proximity to cis-acting elements that promote transcription. This approach has been important in identifying genes that are expressed in a cell type-specific or developmental stage-specific manner. Enhancer trapping, like RFLP/linkage analysis and transposon tagging, identifies genes, not proteins, and it does not directly reveal anything about the nature of the protein product of a gene.

Guest Peptides and Epitope tagging. A number of studies have been performed in which new peptides have been inserted into proteins at a variety of positions by modifying the genes encoding the proteins using recombinant DNA technology. The term 'guest peptide' has been used to describe the foreign peptides in these cases. It is clear that in many cases the presence of such peptides is relatively innocuous and does not substantially compromise protein function—especially in those cases where the peptide is on the surface of the protein rather than in its hydrophobic core.

Epitope tagging is a method that utilizes antibodies against guest peptides to study protein localization at the cellular level and subcellular levels. Epitope tagging begins with a cloned gene and an antibody that recognizes a known peptide (the epitope). Using recombinant DNA technology, a sequence of nucleotides encoding the epitope is inserted into the coding region of the cloned gene, and the hybrid gene is introduced into a cell by a method, such as transformation. When the hybrid gene is expressed, the result is a chimeric protein containing the epitope as a guest peptide. If the epitope is exposed on the surface of the protein, it is available for recognition by the epitope-specific antibody, allowing the investigator to observe the protein within the cell using immunofluorescence or other immunolocalization techniques. Epitope tagging serves to mark proteins of already-cloned genes but does not serve to identify genes.

Isolating Genes Beginning with the Proteins they Encode. A number of procedures have been developed for isolating genes beginning with the proteins that they encode. Some, such as expression library screening, involve the use of specific antibodies that react to the protein of interest. Others involve sequencing all or part of the protein and designing oligonucleotide probes that can be used to identify the gene by DNA/DNA hybridization. In all of these cases, one must have specific knowledge about a protein before it is possible to take steps to clone and characterize the gene that encodes it.

cDNA Cloning and Sequencing. A method of gene identification that has received a great deal of attention in the recent past is the cloning (and in many instances, sequencing) of so-called expressed sequence tags (ESTs) from cDNA libraries made from mRNA extracted from a given tissue or cell type. Information about the proteins encoded by the mRNAs can be derived from the cDNA sequences by identifying and analyzing their open reading frames. In many cases, such cDNAs are not full length, however, and so information about the amino-terminal portion of the protein is lacking. And, more significantly, the method tags transcript sequences and not the proteins that the transcripts encode.

Figure 1:
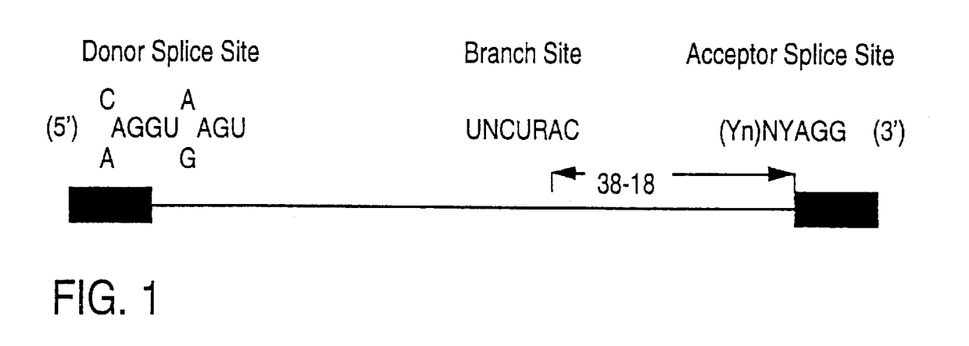

RNA Splicing. RNA splicing is the natural phenomenon, characteristic of all eucaryotic cells, whereby introns are removed from primary RNA transcripts. A large body of research has revealed that an intron is functionally defined by three components—a 5' donor site, a branch site and a 3' acceptor site. If these sites are present, and if the intron is not too large (it can be at least as large as 2 kb in many organisms), and if the distance between the branch and 3' acceptor sites is appropriate, the cellular splicing machinery is activated, and the intron is removed from the transcript. Many different natural DNA sequences are known to have splice site function; consensus sites for mammalian splicing are indicated in FIG. 1. Thus, not only have many active splice sites been cloned, but there is a large database that can be used to design synthetic functional splice site sequences.

Gene Trapping. Gene trapping is a method used to identify transcribed genes. Gene trapping vectors carry splice acceptor sites directly upstream of the coding sequence for a reporter protein, such as β-galactosidase. When the vector inserts into an intron of an actively transcribed gene, the result is a protein fusion between an N-terminal fragment of the target gene-product and the reporter protein, the activity of which is used as an indicator that integration into an active gene has occurred. Gene trapping seeks to identify transcribed genes—not to tag proteins, and to inactivate genes—not to produce an active tagged gene product.

OBJECTS AND ADVANTAGES OF THE INVENTION

"CD-DNA" and "CD-Tagging". The so-called central dogma of genetics states that information flows from DNA to RNA to protein. The method of this invention tags each of the classes of macromolecule included in the central dogma. Accordingly, the method is referred to herein as "CD-tagging". Likewise, the term "CD-DNA" is used herein to refer to a DNA molecule that is inserted into the genome using the method of this invention.

Identifying and Isolating Proteins. RNAs and Genes, A method that allows one to readily identify genes by observing tagged proteins ought to be of great advantage relative to the prior art. CD-tagging has just this feature. In particular, when the protein tag is an epitope that is recognized by a particular antibody, cells can be treated with a CD-DNA, or with DNA constructs containing a CD-DNA, and then subjected to immunological screens or selections to identify the epitope tag. Many different screens or selections are possible, each of which has its own particular advantages. These include direct or indirect immunofluorescence by which tagged proteins can be localized to particular regions or subcellular structures within a cell, immunoblot analysis by which the abundance, molecular weight and isoelectric points of tagged proteins can be determined, enzyme linked immune-assays (ELISAs) by which internal or secreted tagged proteins can be distinguished, and fluorescence-activated cell sorting (FACS) by which living cells with tagged proteins at their surfaces can be obtained.

Once proteins and genes of interest have been identified, they can be efficiently purified using standard hybridization and/or affinity-purification methods that take advantage of their specific tags.

Large Target Size in the Genome. CD-tagging depends on the insertion of a CD-DNA into an intron. Since higher eucaryotic genes contain much more intron than exon sequence, the target size is large relative to any other tagging method in which the DNA must insert into an exon. Further, since the typical gene contains numerous introns, the boundaries of which determine the sites at which amino acid insertions in the protein can be produced by CD-tagging, it is likely that for a given protein there exist multiple sites at which peptide tags produced by CD-DNA insertions would not seriously compromise protein function. Indeed, there is some evidence that the sites in many proteins that are determined by the exon/intron boundaries are particularly likely to be on the surface of the protein—at an ideal location to accept a guest peptide and to allow recognition of that peptide by an antibody.

Hybrid Proteins ire Expressed in Backgrounds where Normal Genes Are Also Present. As discussed earlier, experience has shown that in many, and perhaps most, cases epitope fusion proteins have normal, or nearly normal, activity. But even this is not a requirement in order for CD-tagging to be useful in identifying proteins and their genes because in many applications one or more copies of the normal gene will be present in addition to the tag-containing gene (e.g., when diploid cells are tagged); here the tagged protein need not be fully functional as long as it can, for example, co-assemble at its normal location along with the protein encoded by the unaltered gene.

Obtaining Sequence Data, Once an organism or cell line expressing a protein of interest has been identified using; the method of the invention, a DNA representing a portion of mRNA encoding the protein can be obtained by standard techniques such as plasmid rescue or amplifying the sequence of interest from cDNA by means of the polymerase chain reaction (PCR) using poly-dT as one primer and a DNA complimentary to the tag-encoding sequence as the other. The amplified DNA can then be sequenced by standard methods. Knowledge of the sequence can then be used to design primers for amplification from genomic DNA in order to obtain genomic sequence information.

Application to Analysis of Subcellular Structures. One important application for CD-tagging is to identify proteins, and the genes encoding them, that are present in particular subcellular structures. This can be done by screening CD-DNA recipients for those that express the protein tag in the structure of interest. A significant advantage of this approach is that it does not depend upon the purification of the structure of interest, or even on the prior existence of a method for such purification, as traditional methods for characterizing subcellular structures do.

In addition to identifying proteins in known structures, CD-tagging holds the promise of identifying new structures, and the proteins they contain, that have not been explicitly recognized before.

Application to the analysis of cellular responses. CD-tagging can be used to identify proteins, and the genes encoding them, whose synthesis is stimulated by a particular treatment, such as the administration of a particular hormone or growth factor to a particular cell type. This can be accomplished by comparing treated and untreated cells to identify proteins whose levels change in response to the treatment. And, using standard immunocytochemical methods, one can discriminate among such proteins to identify those that are secreted, localized to the cell surface, or present in particular subcellular compartments.

Application to Virology. Viral infection often leads to specific changes in cellular gene expression. Using CD-tagging, cellular genes whose expression is up or down-regulated can be identified by comparing the levels of tagged proteins in infected versus uninfected cells. Likewise, if the viral genome is tagged, the expression of viral proteins during the viral life cycle can be observed.

Application to Analysis of Transcriptional Regulation. Much genetic regulation occurs at the level of transcriptions. Because CD-tagging puts a unique tag into mRNA species derived from a tagged gene, the tag can be used to investigate mRNA synthesis and stability.

Application to the Analysis of the Human Genome. Because most cellular functions are mediated by proteins, it is of particular interest in the context of the comprehensive analysis of the human genome to identify those parts of the genome that are expressed in the form of proteins. CD-tagging provides an efficient general method to directly identify new genes on the basis of their expression as proteins and on the basis of the location of those proteins in particular cellular or extracellular structures. In addition, CD-tagging provides a method for efficient physical and/or RFLP mapping of genes, as well as a method for the isolation of genes and transcripts via their nucleic acid tags and for the efficient purification of proteins via their epitope tags.

CD-tagging has specific advantages over the prior art method for identifying and mapping genes using expressed sequence tags (ESTs). ESTs are CDNA sequences, not genomic sequences. Thus an EST probe will hybridize not only to the true gene but to any pseudogenes that are present in the genome, thereby limiting its usefulness for mapping and cloning the true gene. Likewise, an EST probe may hybridize with closely related members of a gene family, again limiting its usefulness as a probe for a unique sequence. These limitations do not apply if a gene is identified by CD-tagging, since the method provides direct access, through the CD-DNA tag, to the true gene.

Applications to Medicine. CD-tagging has broad application to the analysis and diagnosis of disease. With regard to analysis, CD-tagging makes it possible to demonstrate, through linkage analysis, that a defect with respect to a given protein represents the primary defect for a given genetic disease or cancer. The function of the protein can then be examined in detail to gain new understanding of the biology of the disease.

With regard to diagnosis, genes that are isolated using CD-tagging can provide probes to identify disease-associated restriction fragment length polymorphisms, and they can provide primers by which mutations responsible for genetic diseases could be precisely identified. Once such polymorphisms or mutations have been identified, diagnostic tests for the presence of mutant alleles in homozygous or heterozygous individuals can be developed using standard approaches. Likewise, proteins that are isolated using the invention can be used as antigens to develop antibodies that can be used to make molecular diagnoses for a particular genetic diseases. With regard to therapy, genes or proteins that are identified using CD-tagging could be used to treat a wide variety of infectious and non-infectious diseases.

SUMMARY OF THE INVENTION

The invention utilizes a "CD-DNA" molecule that contains acceptor and donor sites for RNA splicing. Between the acceptor and donor sites is a sequence of nucleotides that encodes a particular peptide (or set of three peptides, one for each possible reading frame). When the CD-DNA is inserted into an existing intron, it creates a new peptide-encoding exon surrounded by two hybrid, but functional, introns. The result is that, after transcription, RNA splicing and translation, a protein is produced that contains the peptide located precisely between the amino acids encoded by the exons that surrounded the target intron. Thus, in a single recombination event at the DNA level, 1) the gene encoding the protein is tagged by the CD-DNA sequence for recognition by a DNA probe or primer, 2) the RNA transcript encoding the protein is tagged by the peptide-encoding sequence for recognition by a DNA probe or primer, and 3) the protein is tagged by the peptide for recognition by a specific antibody or other reagent.

BRIEF DESCRIPTION OF THE DRAWINGS

FIGS. 2–8 show the structures of a number of DNA molecules that embody the invention. The dark lines represent DNA molecules, with the thicker areas representing coding sequence. Sites in the DNA are represented by short vertical lines. Segments of each DNA are indicated below each molecule. When the DNAs are functioning when inserted into introns, transcription is from left to right for those regions where the sites are shown above the DNA molecules, and from right to left for those regions where the sites are shown below the DNA molecules.

In the figures the various DNA segments ("peptide-encoding segment", "left arm", "right arm", "central segment") are not given specific lengths. This reflects the fact that their lengths can vary considerably and need not have the same values from embodiment to embodiment. The peptide encoding segments will generally be between 24 and 75 nucleotides in length so as to encode peptides of 8 to 25 amino acids; the other segments will generally be between 100 and 1000 base pairs in length so that the hybrid introns created by insertion of the CD-DNA are not too large for efficient splicing. Likewise the base compositions of the various DNA segments are not defined, except at the indicated splice acceptor, branch and donor sites. These segments could be random sequences or be natural sequences without unusual structural features.

It should be emphasized that a great many different molecules of the structures claimed here can be constructed, and that a great many specific means for constructing such molecules using standard recombinant DNA technology will be obvious to an individual skilled in the arts of molecular biology.

DESCRIPTION OF INVENTION

This invention provides a method for tagging proteins and the genes and transcripts that encode them in a single recombinatorial event. The method involves the insertion by in vitro or in vivo recombination of a specially chosen and/or designed DNA sequence into an intron that is expressed within the genome of a cell or organism. This DNA sequence carries: 1) coding information for one or more specific peptides, typically, but not necessarily, from eight to twenty-five amino acids in length, and 2) appropriately placed branch, acceptor and donor sites may represent natural sites taken from known genes or they may be rationally designed based on current knowledge of the nucleotide compositions of such sites.

FIGS. 2 through 8 show the structures of a number of different embodiments of the invention. A key and essential feature of these embodiments is that, when inserted into existing introns, they instruct the splicing machinery of the cell to recognize more than one intron where there was previously one, with these new introns flanking a new exon, or exons, encoding a peptide, or peptides, of determined amino acid sequence.

All of these embodiments can be readily produced by an individual skilled in the arts of molecular biology. I have not specified the specific means by which the embodiments are constructed because there are numerous ways, well known to an individual skilled in the arts of molecular biology, by which this can be accomplished. Likewise, I have not specified the particular nucleotide sequences present in each segment, except as specifically indicated in the text. Again, there are many sequences that could serve and that could be used by one skilled in the arts of molecular biology.

FIG. 1 represents consensus sequences for splicing mammalian pre-mRNA transcripts.

Figure 2:
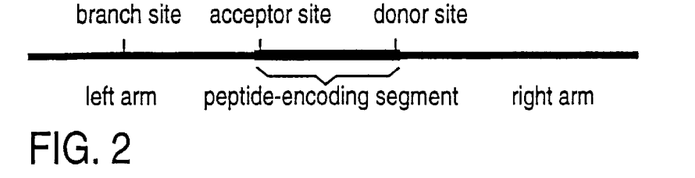

FIG. 2 represents a simple embodiment of the invention. The DNA is designed to function when inserted into an intron that is transcribed from left to right. It has a peptide-encoding segment between splice acceptor donor sites. Within the left arm is a splice branch site. The size and nucleotide sequence of the peptide-encoding region determines the size and amino acid sequence of the encoded peptide, with the amino acid sequence of the peptide determined by the rules of the genetic code. The number of nucleotide pairs in the peptide-encoding region must be an even multiple of three to ensure that the reading frame is maintained with respect to the surrounding exons.

Figure 3:
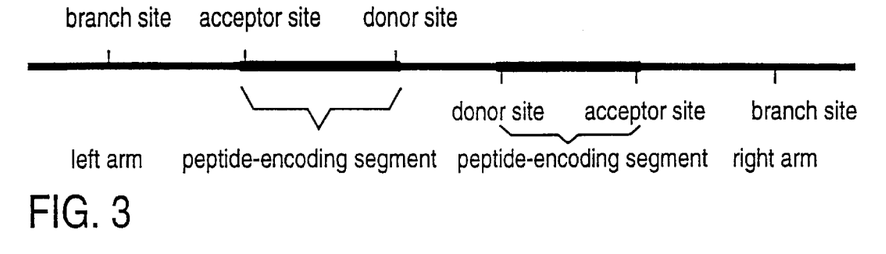
Figure 4:
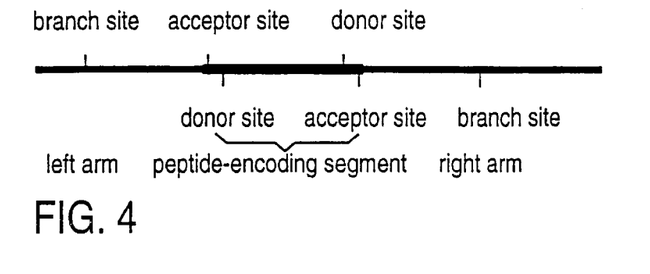
Figure 5:
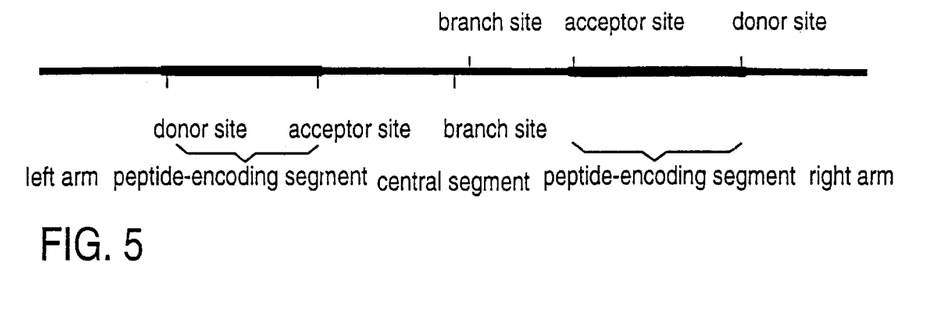

FIGS. 3, 4 and 5 represent embodiments designed to function when inserted into an intron in either orientation.

Figure 6:
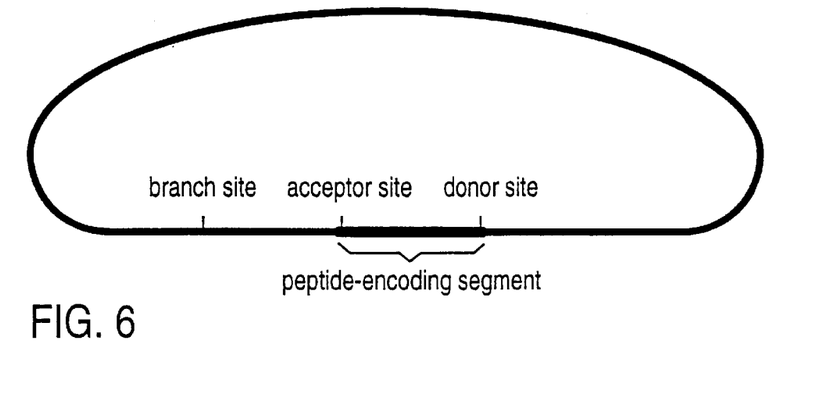

FIG. 6 represents a circular embodiment of the invention. This embodiment could, for example, be a plasmid that contains DNA encoding the guest peptide.

Figure 7:
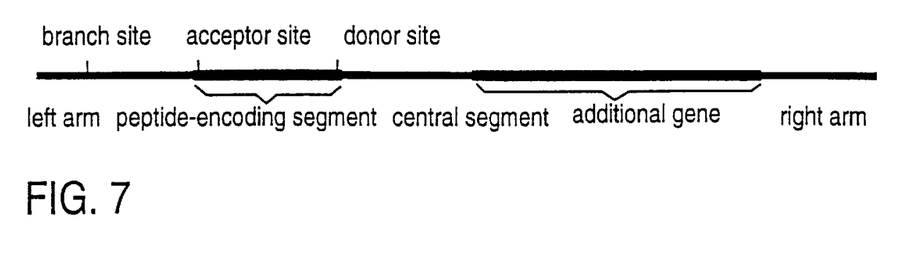

FIG. 7 represents an embodiment incorporating a gene, or genes, that could allow for selection in a target cell. The gene is intron-less so that it does not contribute splice sites.

Figure 8:
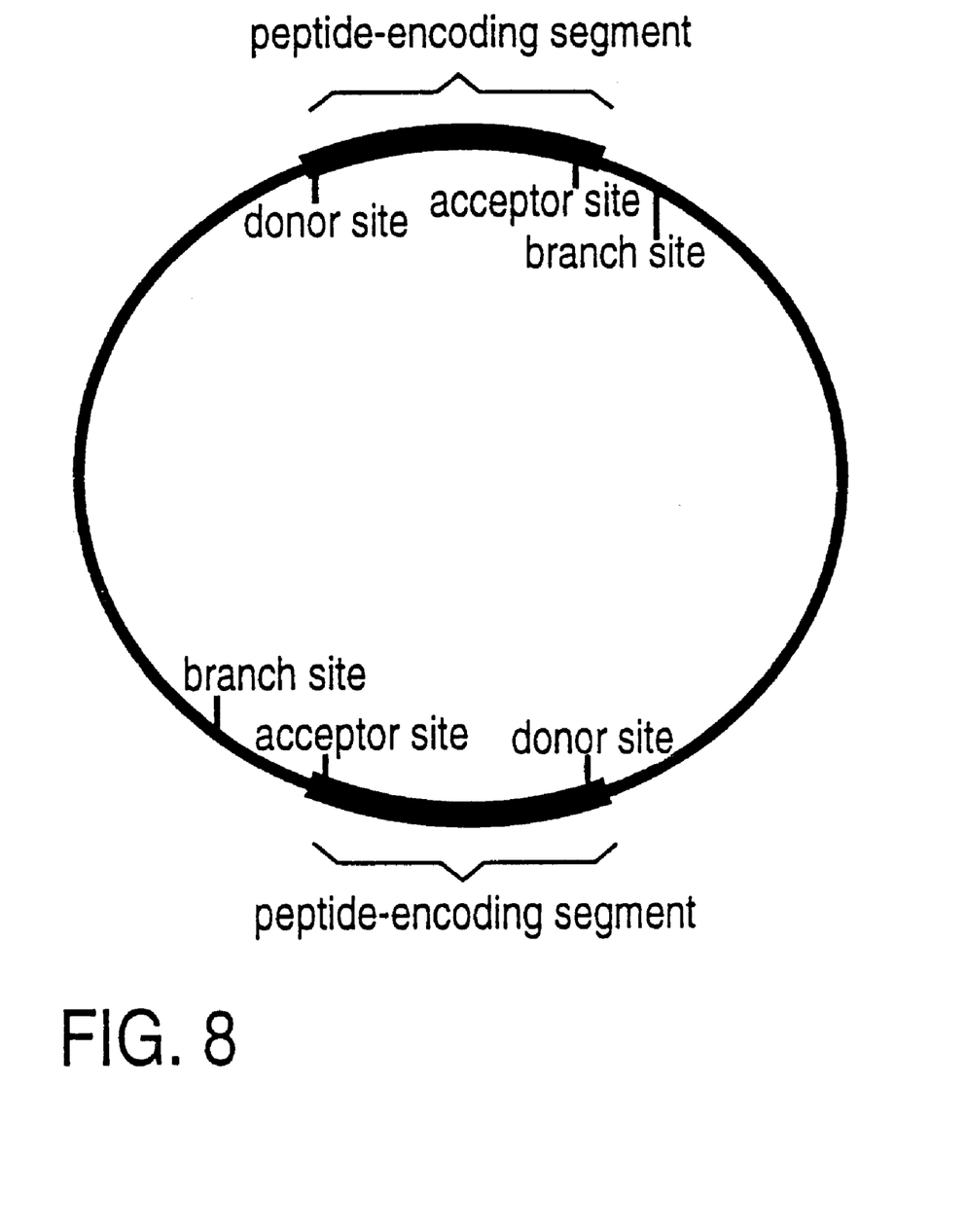

FIG. 8 represents a circular embodiment of the invention containing two peptide-encoding segments.

Figure 9:
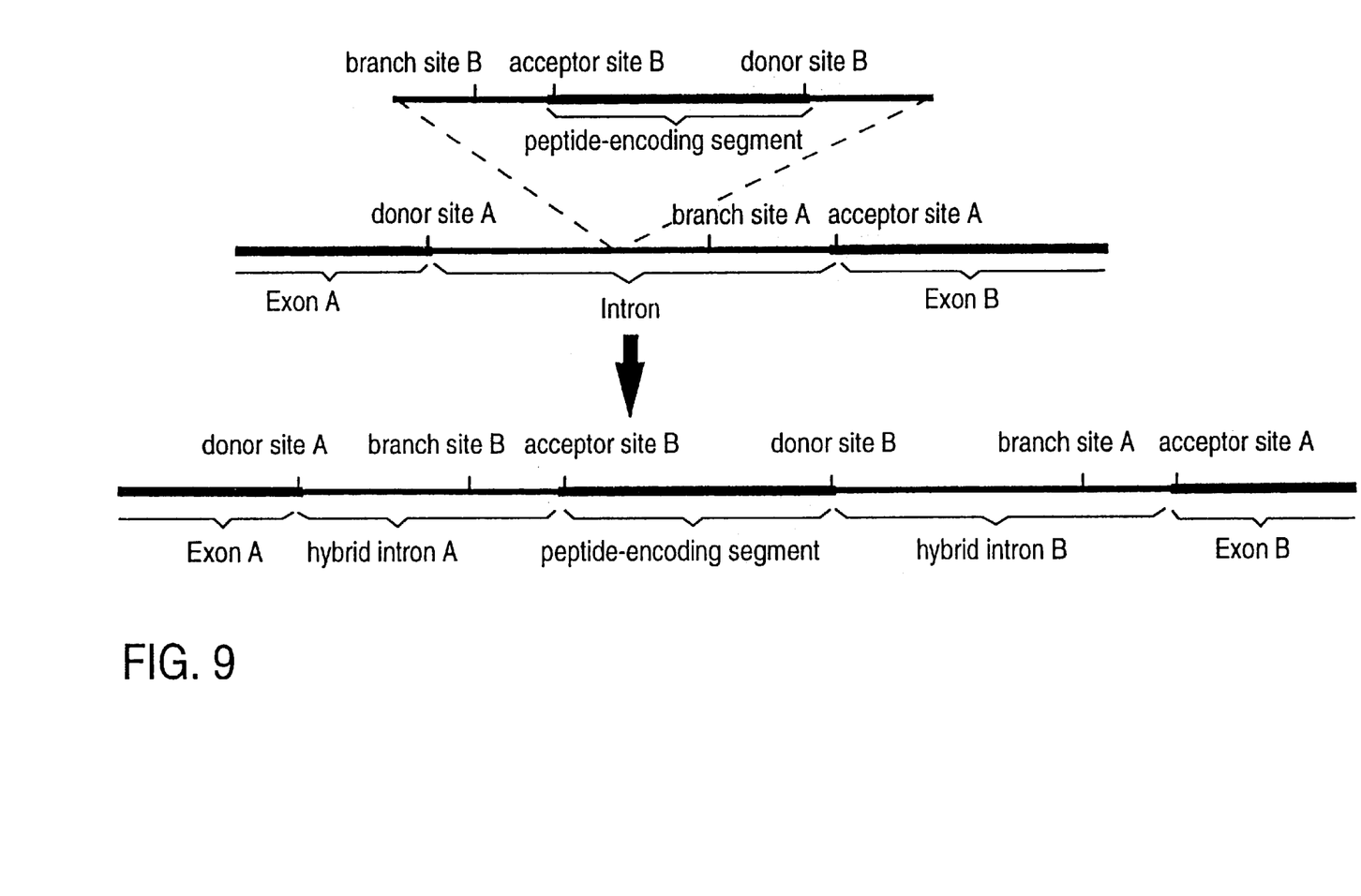

FIG. 9 represents the structure of CD-DNA (embodiment 1) inserted into the intron.

Figure 10:
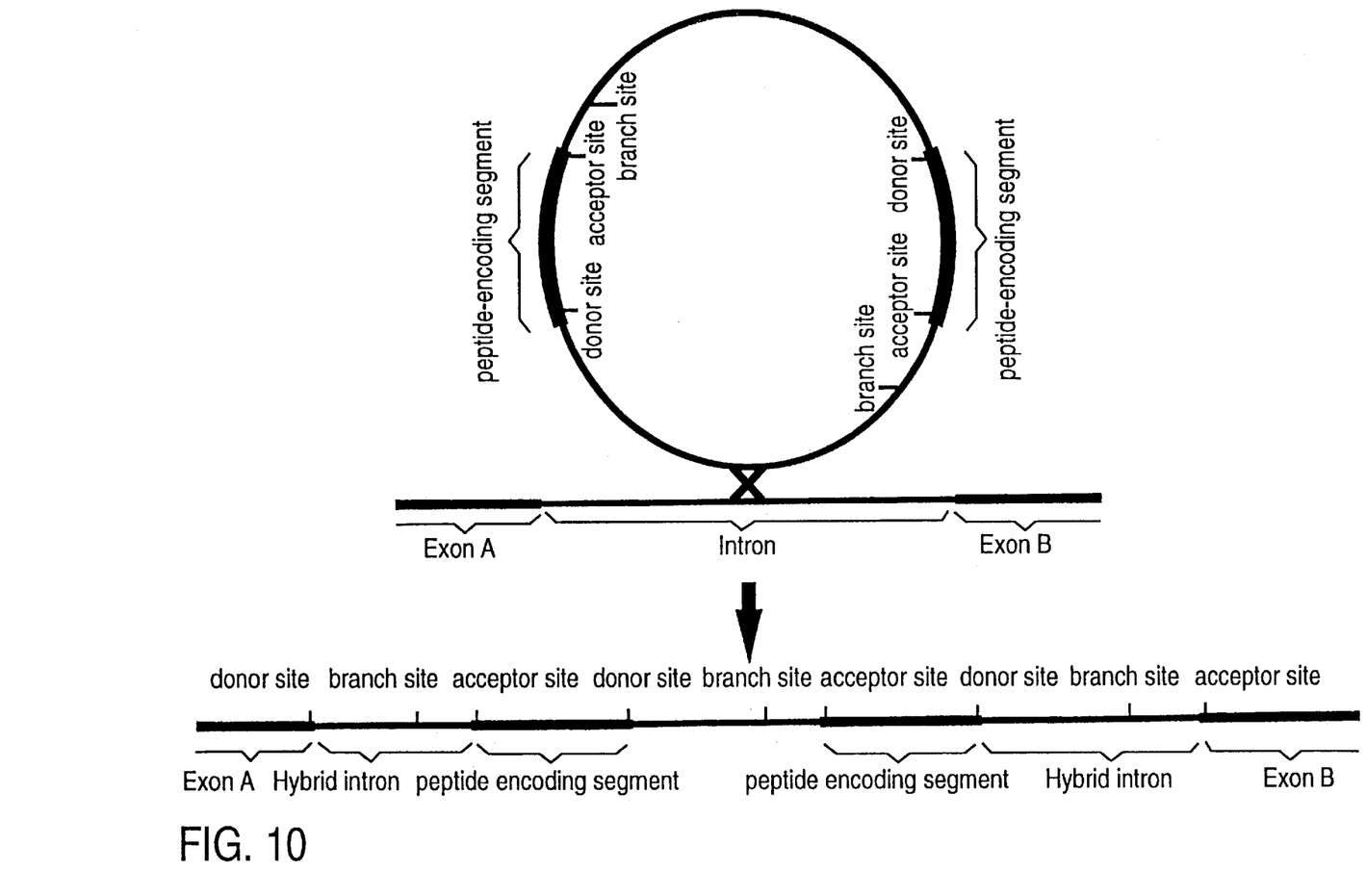

FIG. 10 represents the structure of CD-DNA (embodiment 8) inserted into an intron.

FIGS. 2 through 8 represent some, but by no means all, possible embodiments of the invention. More complex embodiments that retain the essential elements of the invention are also possible. For example, CD-DNAs containing more than two segments encoding guest peptides can be designed; such CD-DNAs could be relatively large and yet not lead to the generation, in the target gene, of new introns that are excessively large for efficient splicing.

Likewise, it may be, for example, that in certain cells the branch sites are less critical to splicing function than the acceptor and donor sites, in which case an effective embodiment of the invention might be created without specific branch sites. Thus, as knowledge of the biochemistry of RNA splicing accumulates in the art, DNA sequence features may be identified that can increase the efficiency of CD-tagging. The scope of this invention is intended to include such features.

OPERATION OF THE INVENTION

The design of the CD-DNA is such that when it is inserted into an existing intron, it creates, within the intron, a new peptide-encoding exon. The result is that, after transcription, RNA splicing and translation, a protein is produced that contains the peptide located precisely between the amino acids encoded by the exons that surrounded the target intron. Thus, in a single recombination event: 1) the gene encoding the protein is tagged by the CD-DNA sequence for recognition by a DNA probe or primer, 2) the RNA transcript encoding the protein is tagged by the peptide-encoding sequence for recognition by a DNA probe or primer, and 3) the protein is tagged by the peptide for recognition by a specific antibody or other reagent

Delivery, Recombination and Function of CD-DNAs

Recombination of a CD-DNA within an intron is essential to successful CD-tagging. FIGS. 9 illustrates the structure of the DNA that results from the integration of a linear CD-DNA within an intron by recombination at its ends. When transcribed, this DNA yields an RNA that is spliced to produce an mRNA encoding a protein that contains a guest peptide located precisely between the protein segments encoded by the exons that bound the target intron. FIG. 10 illustrates the structure of the DNA that results from the integration of a circular CD-DNA within an intron by a single crossover. When transcribed, this integrated DNA yields an RNA that is spliced to produce an mRNA encoding a protein that also contains a guest peptide (in this case encoded in two guest exons) located precisely between the protein segments encoded by the exons that bound the target intron.

Integration of a CD-DNA can be accomplished in a number of ways. One approach involves the introduction of CD-DNA into cells by standard methods such as transformation, electroporation, transfection, bulk loading, or liposome fusion, followed by nonhomologous recombination of the CD-DNA into the genome. The occurance of such recombination is well known in many cell types; sometimes the integration of foreign DNA is accompanied by a small deletion of the target sequence, but, as long as such a deletion remains within the intron, it will present no problem. In another approach, the CD-DNA is inserted by standard recombination methods into a genomic library in a viral or plasmid vector, and the recombinant plasmids or viruses are then introduced into cells where the recombinant genes are expressed. Yet another approach takes advantage of the mobility of transposons; in this case the CD-DNA is located on a transposon that moves it to new sites in the genome via transposon insertion.

Peptides and Epitopes

In one major class of application of CD-tagging, the peptide that is introduced into a protein is an epitope that is recognized by a specific monoclonal or polyclonal antibody. In principle, almost any amino acid sequence not present in the cells of interest could serve as such an epitope. And, while there may not be a single "optimal" epitope, epitope design could still follow a rational basis. In most cases, it would be valuable for the epitope to be on the surface of the protein where 1) it would be readily available to the antibody combining site, and 2) it would minimally disrupt the tertiary structure of the protein as a whole. Surface location can be promoted by use of hydrophilic epitopes (except in the case of integral membrane proteins, where hydrophobic epitopes can be employed). If a single repeating nucteotide is used to encode the epitope, it will yield the same poly-amino acid epitope in all three reading frames; a repeating dinucleotide will encode two potential poly-amino acid epitopes, and a repeating trinucleotide, three such epitopes. A somewhat more complex repeating sequence can be used to encode repeating di-amino acid epitopes, and still more informationally complex sequences can be used to create epitopes of a very wide variety of amino acid sequences, with the only obvious requirement being the absence of stop codons in the reading frames. Furthermore, some CD-DNAs (FIGS. 3,4,5) contain peptide-encoding sequences that can be read in both directions; in these cases as many as six distinct epitopes can be encoded on the same CD-DNA. Which epitope appears in the protein will then depend on the orientation the CD-DNA as well as the the reading frame that is is dictated by the specifics of the intron/exon boundaries of the target intron.

In addition to using epitopes that are designed according to the principles outlined above, other epitopes exist, such as hemaglutinin sequences from influenza virus, micro-exon 1 encoded sequence from the ubx gene of Drosophila, or sequences encoded by the myc oncogene, that have already proved their worth in epitope tagging. These very sequences can be used in embodiments of CD-tagging, thereby ensuring that the guest peptides can be identified by standard procedures.

Recipient Cell

Because RNA splicing is a universal characteristic of eucaryotic cells, CD-tagging is applicable to a very wide variety of cells and organisms, including yeasts, protozoans, algae, metazoans (both plant and animal), and somatic and germline cells derived from metazoan organisms. Because the nucleotide sequences that are necessary and sufficient for splicing are highly conserved across the eucaryotes, it is likely that in many cases the same CD-DNA will function in a variety of cell types and organisms. This is not to say, however, that a given CD-DNA will not function optimally in a given cell type or organism, and so it may prove useful to develop different CD-DNAs for use in different backgrounds. It is also the case that the signals for alternative splicing may vary from cell to cell; the optimal CD-DNA would typically be one in which splicing of the hybrid transcript always occurs. One way to maximize the liklihood of this is construct the CD-DNA using nucleotide sequences that are known to function in the very background in which the tagging is to be performed.

Identification of Genes and Proteins

Once cells or organisms have been constructed by insertion of the CD-DNA sequence into the genome, or by insertion into a library that is then transferred to the genome, they can be screened with epitope-specific antibodies by standard immunological techniques. These techniques include ELISAs and western blots to identify cells in which hybrid proteins are synthesized, and immunofluorescence, immunoelectron microscopy and other immunocytochemical methods to identify the cellular and sub-cellular locations of the epitope-containing hybrid proteins. When cells or organisms carrying immunoreactive proteins in structures of interest have been identified, the epitope tags in the proteins can be used to purify them by standard affinity-based methods, and/or the epitope-encoding polynucleotide tags can be used to identify and/or sequence cDNAs made from cellular MRNA by standard methods, and/or the vector tags in the DNAs can be used to clone the genes by standard methods and/or to obtain DNA sequence data.

Conclusion, Ramifications and Scope of Invention

In conclusion, this invention describes a method for tagging gene, transcript and protein in a single recombinational event This method has unique and highly useful advantages over all other methods with similar aims in the prior art.

The specific description of my invention presented above should not be construed as limiting its scope, but rather as exemplification of certain embodiments thereof. Many other variations and applications are possible. For example, peptides could be designed that have sites that lead to specific covalent modification of the tagged protein—either by a small molecule or a macromolecule. Or the peptide tag could contain a site for hydrolysis of a peptide bond by an inducible pro tease, thereby making it possible to assess the function of the tagged gene in vivo. Or CD-DNAs could contain cis-acting sites for the inducible activation of transcription arranged so that inhibitory anti-sense transcripts from the target gene are produced, thereby making it possible to assess the function of the tagged gene in vivo. Or the peptide-encoding sequence could contain nucleotides that are hypermutable in vivo so as to promote mutations such as frameshifts that could inactivate protein function. Or an enhancer of transcription could be included within the CD-DNA so that expression of the target gene is stimulated by the CD-DNA. Accordingly, the scope of the invention should be determined not by the embodiments illustrated here but by the appended claims and their legal equivalents.

I claim:

1. A eucaryotic cell containing at least one gene tagged in accordance with the method comprising (1) producing a tagged gene by inserting a DNA sequence into an intron of a gene by:

(a) selecting a DNA sequence:

(i) having a 5' portion free of any nucleotide sequence selected from the group consisting of CAGGTAAGT, CAGGTGAGT, AAGGTAAGT, AAGGTGAGT, followed by;

(ii) a nucleotide sequence selected from the group consisting of TACTAAC, TGCTAAC, TCCTAAC, TCCTAAC, TACTGAC, TGCTGAC, TCCTGAC, TTCTGAC and TACTAAC and any nucleotide sequence identical to a known splice branch site in a known gene, followed by;

(iii) a sequence selected from the group consisting of a sequence 14 to 34 nucleotides in length and any nucleotide sequence identical in length to a known spacer region between splice branch and acceptor sites in a known gene, followed by;

(iv) a nucleotide sequence selected from the group consisting of CAGG, TAGG, and any sequence identical to a known splice acceptor site in a known gene, followed by;

(v) an open reading frame encoding a known peptide tag recognizable by a known reaction characteristic of said known peptide tag, followed by;

(vi) a nucleotide sequence selected from the group consisting of CAGGTAAGT, CAGGTGAGT, AAGGTAAGT, AAGGTGAG and any sequence identical to a known splice donor site in a known gene; and     (b) inserting said DNA sequence into said intron within said gene to create a tagged gene; and (2) incubating said tagged gene within a eucaryotic cell so as to maintain intact or to introduce said tagged gene within the genome of said eucaryotic cell.

\* \* \* \* \*